United States Patent
Reese

(10) Patent No.: US 10,485,946 B2
(45) Date of Patent: Nov. 26, 2019

(54) PERSONAL HEALTH DEVICE

(71) Applicant: Harvey Reese, Philadelphia, PA (US)

(72) Inventor: Harvey Reese, Philadelphia, PA (US)

( * ) Notice: Subject to any disclaimer, the term of this patent is extended or adjusted under 35 U.S.C. 154(b) by 688 days.

(21) Appl. No.: 15/295,923

(22) Filed: Oct. 17, 2016

(65) Prior Publication Data

US 2017/0028156 A1 Feb. 2, 2017

Related U.S. Application Data

(63) Continuation of application No. 13/911,795, filed on Jun. 6, 2013, now abandoned.

(51) Int. Cl.
| | | |
|---|---|---|
| A61M 16/10 | (2006.01) | |
| A62B 7/10 | (2006.01) | |
| A61M 16/00 | (2006.01) | |
| A61L 9/20 | (2006.01) | |
| A45F 5/00 | (2006.01) | |
| A61J 1/03 | (2006.01) | |

(52) U.S. Cl.
CPC ............ *A61M 16/105* (2013.01); *A45F 5/00* (2013.01); *A61J 1/03* (2013.01); *A61L 9/20* (2013.01); *A61M 16/0066* (2013.01); *A61M 16/1005* (2014.02); *A62B 7/10* (2013.01); *A61L 2209/14* (2013.01); *A61M 2205/053* (2013.01); *A61M 2205/584* (2013.01); *A61M 2205/8206* (2013.01)

(58) Field of Classification Search
CPC .......... A61M 16/105; A61M 2205/584; A61M 2205/8206; A62B 7/10; A62B 18/003; A61L 2209/14
USPC ...................................................... 128/200.27
See application file for complete search history.

(56) References Cited

U.S. PATENT DOCUMENTS

| | | | | |
|---|---|---|---|---|
| 4,256,694 | A * | 3/1981 | McAllister | G01N 31/224 422/416 |
| 4,971,052 | A * | 11/1990 | Edwards | A62B 18/006 128/205.12 |
| 5,697,841 | A * | 12/1997 | Di Giovine | F24F 13/065 454/286 |
| 5,749,359 | A * | 5/1998 | Hansen | A62B 9/003 128/201.25 |
| 7,815,334 | B2 * | 10/2010 | Sherman | A45F 5/00 224/219 |
| 7,828,524 | B2 * | 11/2010 | Chen | F04D 25/084 415/206 |
| 2003/0086831 | A1 * | 5/2003 | Horton, III | A61L 9/205 422/120 |

(Continued)

*Primary Examiner* — Colin W Stuart
*Assistant Examiner* — Douglas Y Sul
(74) *Attorney, Agent, or Firm* — Michael J. Faycik, Jr.

(57) ABSTRACT

A portable device provides filtered air to the face of a user, and has a housing having an air outlet disposed to direct air toward a face of a user, a fan disposed inside the housing for urging air toward the air outlet, a filter member disposed in the air outlet, and an air inlet. A UV light source is provided inside the housing, for providing UV light to purify air moving inside said housing toward said filter member. A CO detector disk is mounted on an outside wall of the housing, for providing a visible color change when CO is detected. A pill box is mounted on an outside wall of the housing, as well as a holder for a personal medications log mounted, and a personal medications log insertable therein.

5 Claims, 16 Drawing Sheets

(56) References Cited

U.S. PATENT DOCUMENTS

| | | | | |
|---|---|---|---|---|
| 2004/0146437 A1* | 7/2004 | Arts | ............ | A61L 2/10 |
| | | | | 422/186.07 |
| 2007/0163588 A1* | 7/2007 | Hebrank | ............ | A61L 9/16 |
| | | | | 128/204.18 |
| 2011/0100221 A1* | 5/2011 | Wu | ............ | B01D 46/0024 |
| | | | | 96/16 |

* cited by examiner

PERSONAL HEALTH DEVICE

CROSS REFERENCE TO RELATED APPLICATIONS

Not applicable.

STATEMENT REGARDING FEDERALLY SPONSORED RESEARCH OR DEVELOPMENT

Not applicable.

FIELD OF THE INVENTION

The present invention relates to personal health devices for protecting a user, and to portable devices for providing filtered air for breathing by a user.

BACKGROUND OF THE INVENTION

It is a problem in the art to provide filtered air for breathing by a user. It is also a problem in the art to provide a portable device for providing filtered air to a user.

One prior art solution includes simple surgical masks to filter air which is breathed by a wearer. However, such masks have drawbacks, not the least of which is that the face is covered. And, such masks suffer from leakage, and the filtering material must generally be thin to permit ready breathing which therefore diminishes the filtering effects. Other solutions to providing filtered air have not been portable, such solutions including use of fixed hardware such as air purifiers and air conditioning units.

Additionally, purifying air is known, but usually requires heavy equipment such as that used in hospitals.

There is a need for a portable device to provide filtered air to a user. There is additionally a need for a portable device that is convenient, light in weight, and low in cost, to provide filtered air to a user. Further, there is a need for a portable device to provide purified air to a user.

SUMMARY OF THE INVENTION

From the foregoing, it is seen that it is a problem in the art to provide a device meeting the above requirements. According to the present invention, a device is provided which meets the aforementioned requirements and needs in the prior art. Specifically, the device according to the present invention provides a portable device to provide filtered air to a user. The device further provides a portable device that is convenient, light in weight, and low in cost, to supply filtered air to a user. Further, the device of the present invention provides a portable device to provide purified air to a user.

The device according to the present invention includes a fan inside a housing, the housing having an air outlet portion for directing air to connections for a neck strap or chain to permit wearing of the housing by a user, an air inlet for the fan, and a filter disposed in the air outlet portion of the housing to filter air directed toward the face of the user.

An advantage of the present invention is that the user can breathe air that is relatively free of pollen, smoke particles, and dust. The device of the present invention can form an air curtain or air shield in front of the face of the user, that substantially blocks the ambient unfiltered air from reaching the face of a user.

Advantageously, the device according to the present invention also includes an embodiment which has an air purifying feature. A UV light is disposed inside the housing, which affects bacteria and viruses. A sufficiently strong UV light source is known to neutralize or destroy such bacteria and viruses. The air purifying feature of this embodiment of the present invention is useful for situations where there may be an outbreak of a virus outbreak or a bacteria outbreak.

Other objects and advantages of the present invention will be more readily apparent from the following detailed description when read in conjunction with the accompanying drawings.

DETAILED DESCRIPTION OF THE INVENTION

Figure 1:
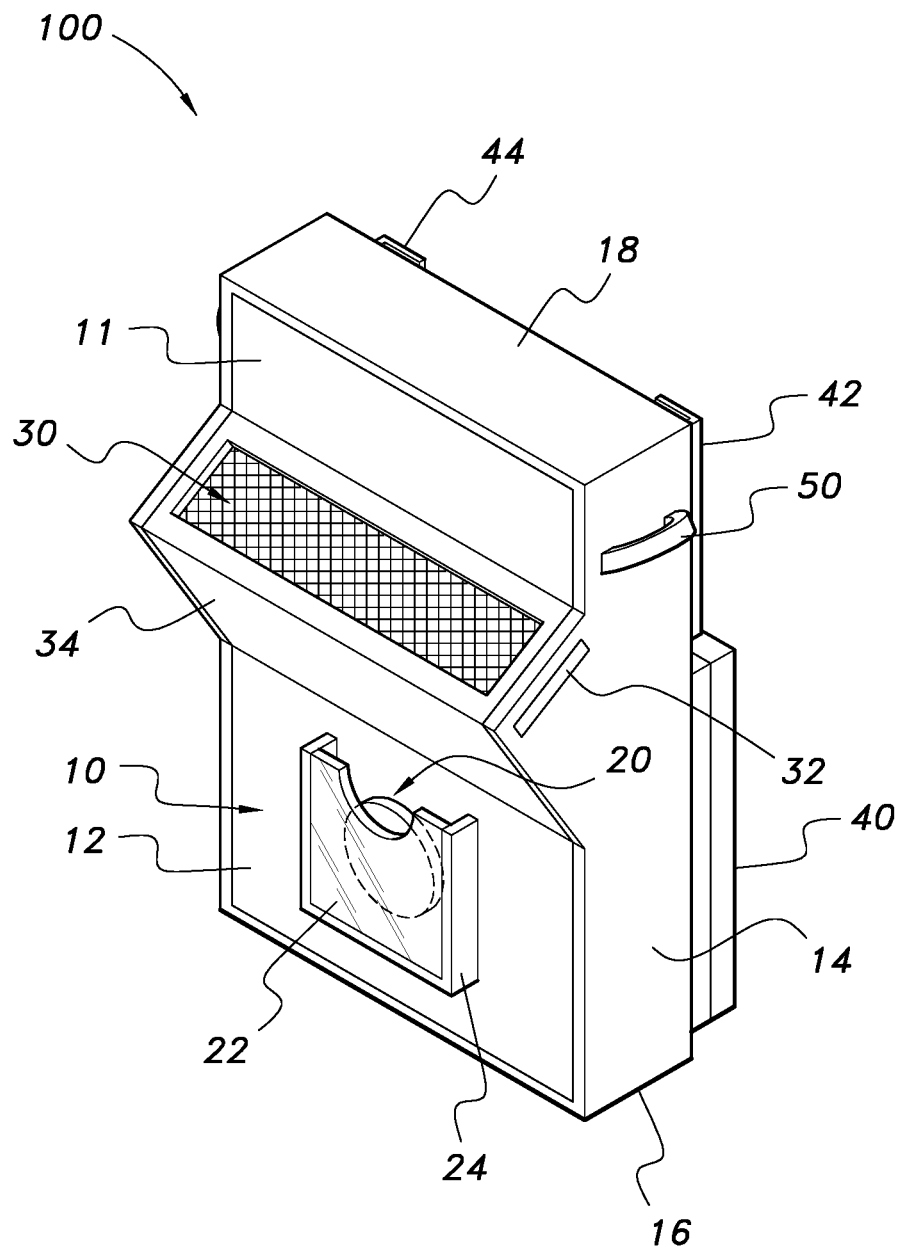
FIG. 1 is a front elevational view of a personal health device according to the present invention.

FIG. 1 is a front elevational view of a personal health device 100, which has a housing 10 and an air outlet portion 30. The housing 10 includes an upper front panel 11, a lower front panel 12, a side panel 14, a lower panel 16, a top panel 18, and a pair of extending connector portions 50 (only one of which is visible in FIG. 1). A filter 32 is disposed in the air outlet portion 30, for filtering air.

In FIG. 1, the air outlet portion has an angled lower panel 34. The air filter 32 fits through a slot (unnumbered) in the side wall 14. The opposite side wall is similar to side wall 14, and therefore the air filter is supported in two opposed slots in the opposed side walls.

A compartment 40 is disposed on the rear of the device 100, which serves as a compartment for pills, tablets, capsules, and the like, which are typically used for medications. Also, support members 42 and 44 are visible, which are parts of a structure (shown in FIG. 7) used for receiving a personal medications log 88 (also shown in FIG. 7).

A CO detector disk 20 is provided which changes color when exposed to CO gas. The CO detector disk 20 is supported by the lower front panel 12, a wall 24 connected to the panel 12, and a transparent cover portion 22. The CO detector disk 20 is removable from an opening at the top which is not bounded by the wall 24. Any known type of CO detector material can be used for the CO detector disk 20. In a preferred embodiment, the CO detector disk 20 is yellow in a normal condition, and changes color to black when CO is detected.

Figure 2A:
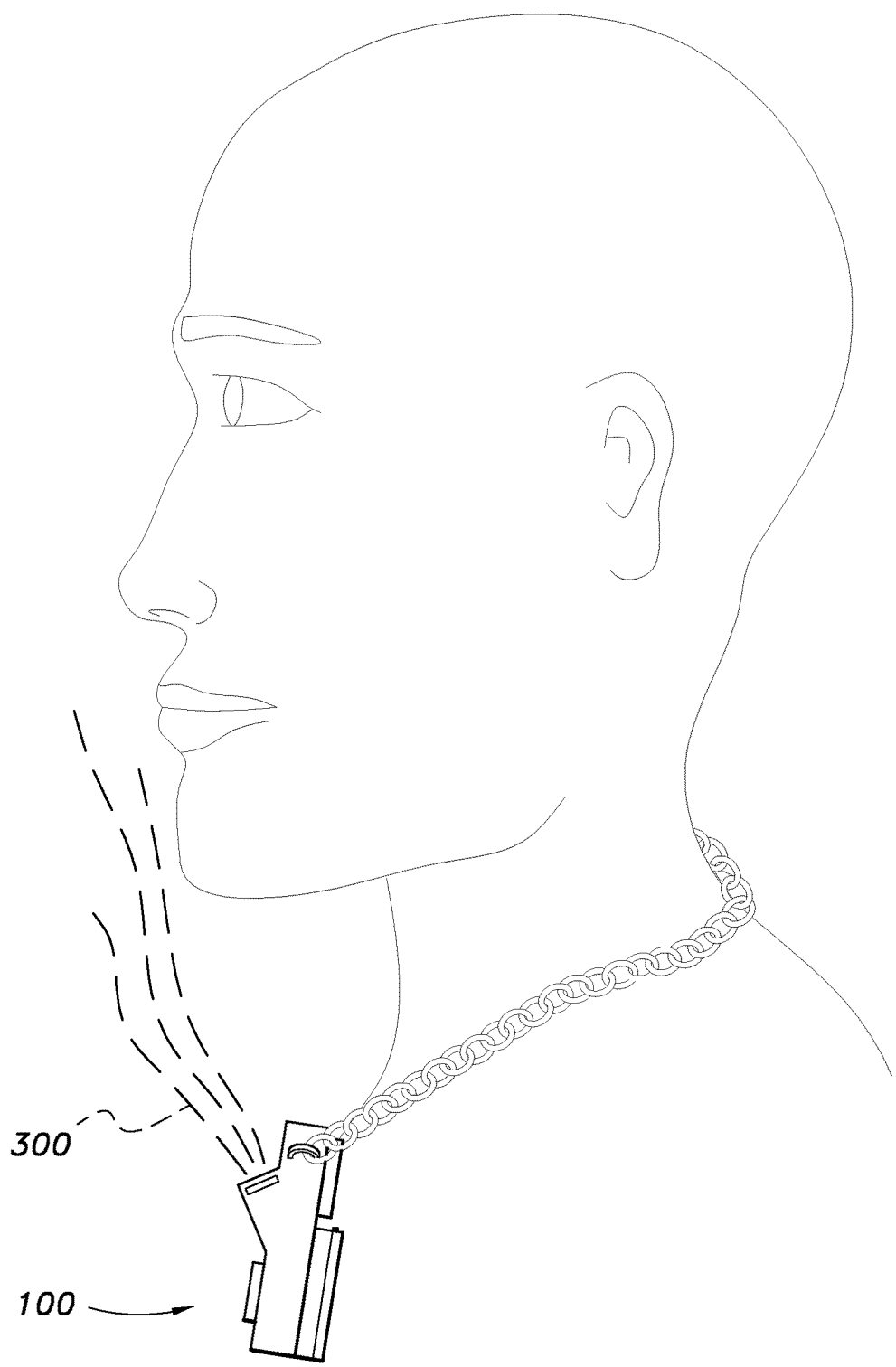
FIG. 2A is a side elevational schematic view of the device of FIG. 1 providing an air supply to the face of a user.

FIG. 2A is a side elevational schematic view of the device 100 of FIG. 1 providing an air supply 300 to the face of a user. The air supply 300 is seen as providing an air curtain in front of the mouth and nose of the user, tending to keep unfiltered air away and providing filtered breathing air to the user. In FIG. 2A, the device 100 is supported on a chain (unnumbered), though it is also contemplated that a strap, string, or other supporting member can be used to provide a convenient way for the user to carry the device 100 is a position suitable for use.

Figure 2B:
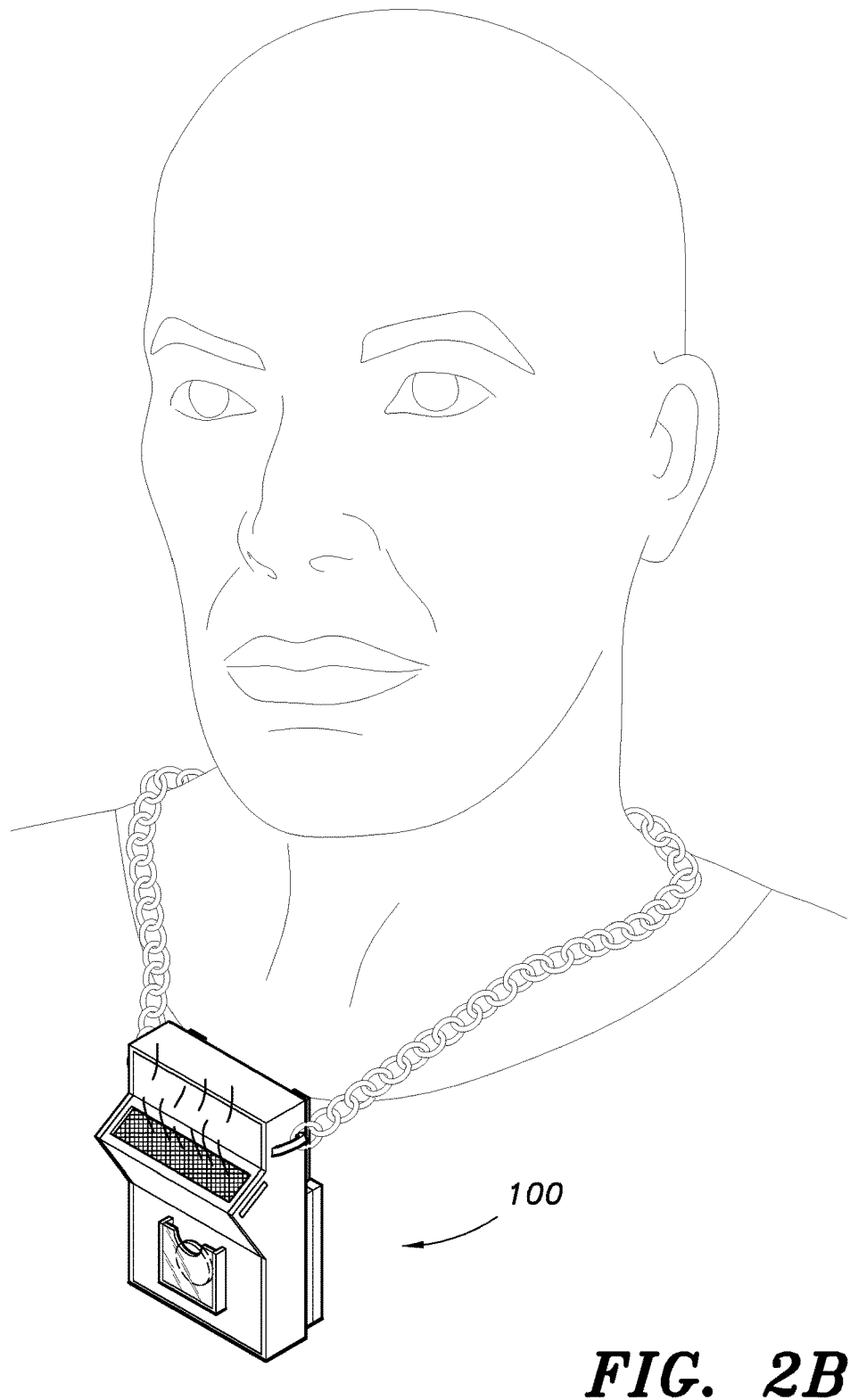
FIG. 2B is a front elevational schematic view of the device of FIG. 1 providing an air supply to the face of a user.

FIG. 2B is a front elevational schematic view of the device of FIG. 1 as worn by a user, as described above with reference to FIG. 2A, for providing an air supply to the face of a user.

Figure 3:
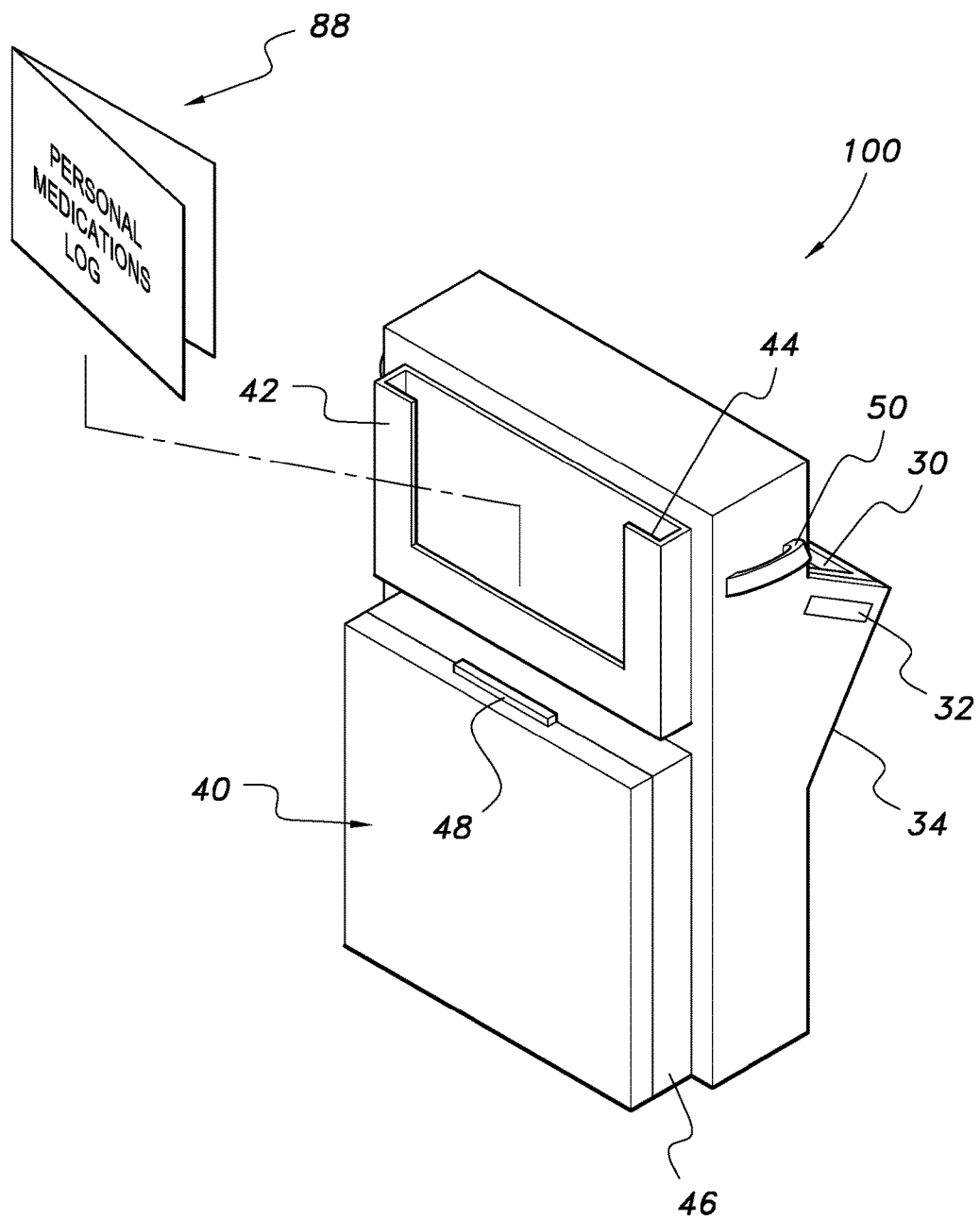
FIG. 3 is an elevational view of the device of FIG. 1 showing a rear side of the device.

FIG. 3 is an elevational view of the device of FIG. 1 showing a rear side of the device. The compartment 40 has been described in the above, and further includes a latch portion 48 and a sidewall 46. The personal medications log 88 (also shown in FIG. 7) is shown for insertion into a support portion formed by the portions 42 and 44 which are connected by a bottom portion (unnumbered).

Figure 4:
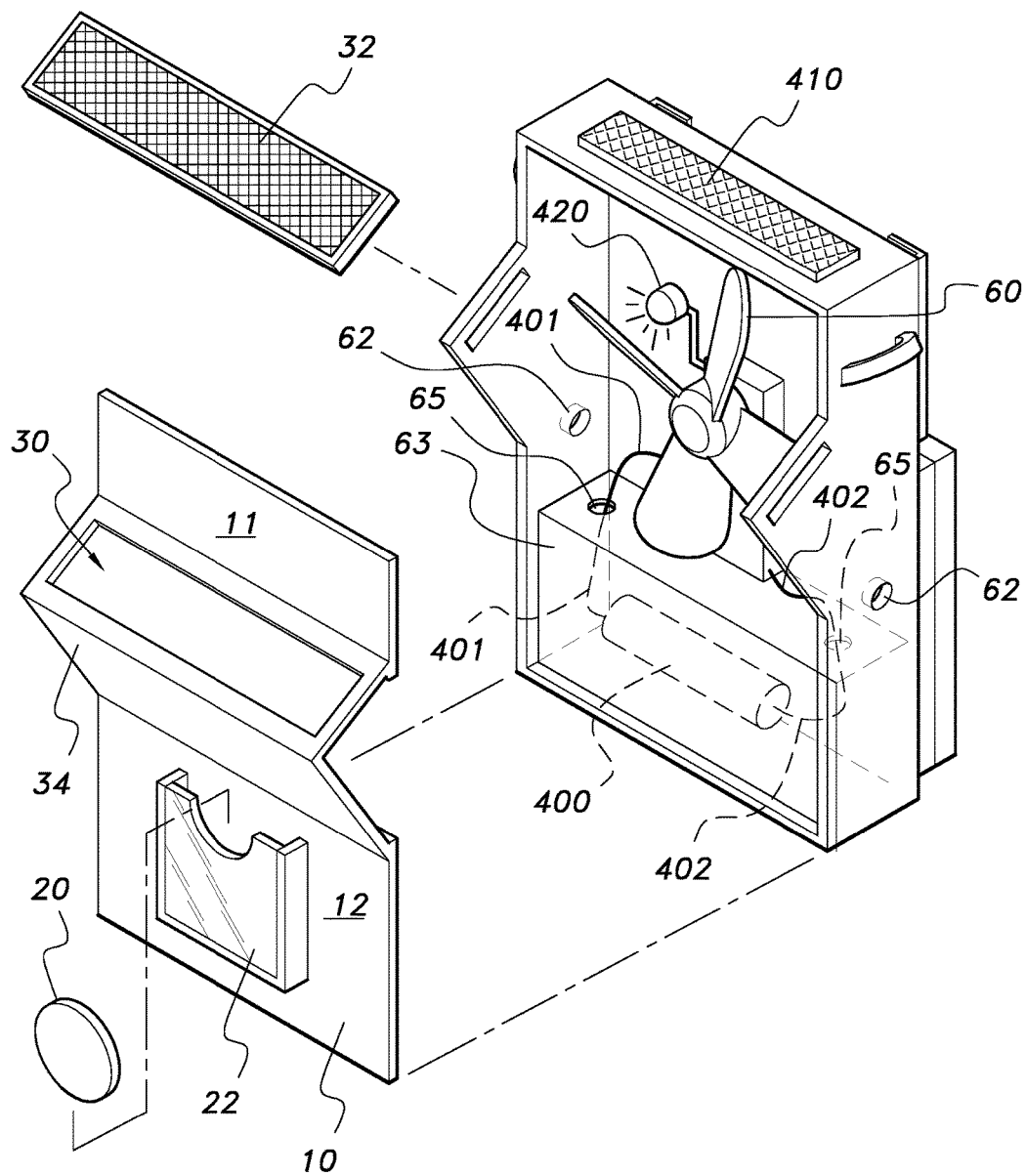
FIG. 4 is an assembly view of the device of FIG. 1.

FIG. 4 is an assembly view of the device 100 of FIG. 1. In this view, like numbered elements as in FIG. 1 are as described above. Additionally, FIG. 1 shows a fan 60, a power source 400, and air passages 62, 62. The fan 60 can be a pad fan, for example. The air passages 62, 62 are merely schematic, and in practice, a greater number of such air passages would usually be provided, which may be smaller or larger than those shown, and which may be located in places other than or in addition to those shown. All such variations would be within the ambit of skill of any one having skill in the fan and fan housing arts, and all such variations are contemplated as being within the scope of the present invention.

Other elements and features are shown in FIG. 4. The filter 32 is shown separately, and a solar panel 410 (which is optional) is disposed on top of the housing. The solar panel may be used to power the fan, or to act as a booster to extend battery life in use, or as a way of recharging the battery 400 when the device 100 is not in use. It is noted that an ON-OFF switch is not shown, and such ON-OFF switches are very well known. The ON-OFF switch is therefore omitted for the sake of clarity. It would be conventional to provide and use such an ON-OFF switch at any convenient location, and all such variations are considered to be within the scope of the present invention. The device 100 can also be turned OFF by manually removing the battery 400.

A UV light source 420 is schematically depicted in this view, being connected by a pair of wires (unnumbered) to a power supply. A battery 400 is shown, having two connecting wires 401 and 402 schematically shown being connected with the based of the fan 60, for supplying power to the fan 60. The fan 60 itself is contemplated as being a conventional bladed fan.

The UV light source 420 is provided to purify and sterilize air, by emitting UV light on air that is being urged by the fan 60 toward the filter 32. The UV light source 420 is optionally included, and when so included it is contemplated that interior surfaces of the housing have a UV-reflecting coating or are composed of UV-reflecting material, to enhance and improve the effectiveness of the UV light. While a single UV light source 420 is shown and positioned in FIG. 4, it will be understood that this is for illustrative purposes, and in practical use one or more such UV light sources can be provided, and their locations selected for improved effectiveness. It will be understood that all such variations would be within the ambit of skill of any one having skill in the art of UV light sources for use in purifying air.

In the following, it will be understood that different types of fans and housings can be used, and different types of materials, power sources, and filter types can be used. All such variations would be within the ambit of skill of anyone having skill in the fan and fan housing arts, and all such variations are contemplated as being within the scope of the present invention.

Additionally, materials, paints, and colorings can be varied. Power sources can also be varied, including disposable batteries, rechargeable batteries, high capacity cell phone batteries, solar-power films and/or panels, solar-rechargeable batteries, and so on. The position and number of the air holes can be varied, the number and placement of UV light sources can be varied, and the location of the CO detector can be varied. All such variations are contemplated as being within the scope of the present invention.

Figure 5:
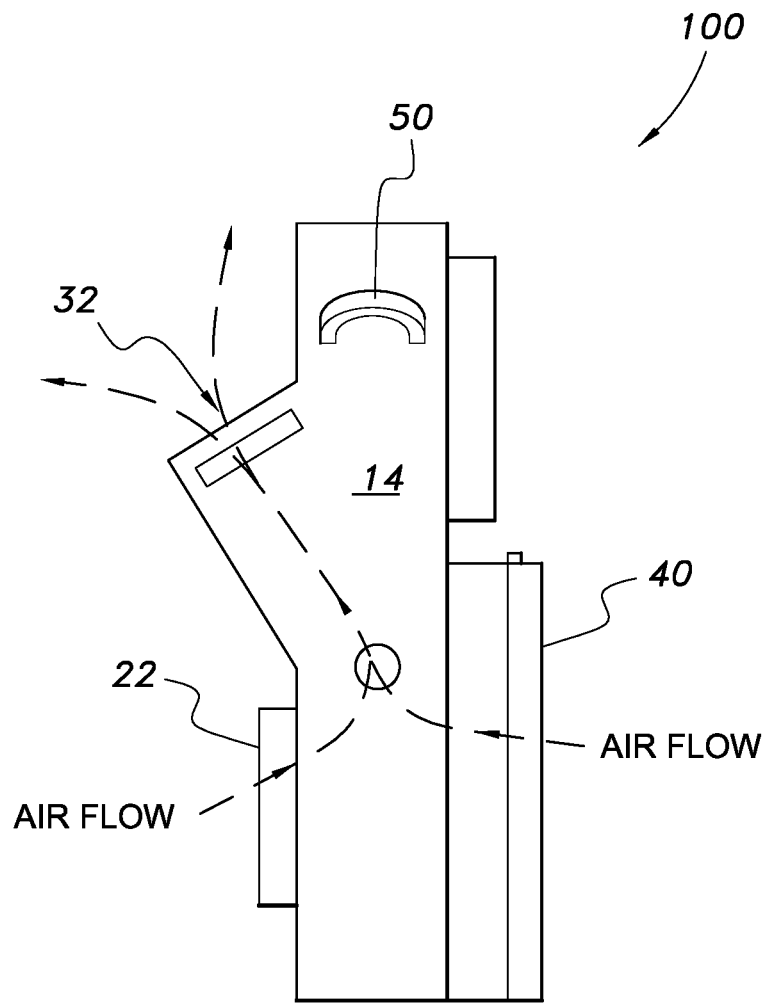
FIG. 5 is a side elevational view of the device of FIG. 1 as viewed from the right.

FIG. 5 is a side elevational view of the device 100 of FIG. 1 as viewed from the right. The air flow path is schematically illustrated in this view.

Figure 6:
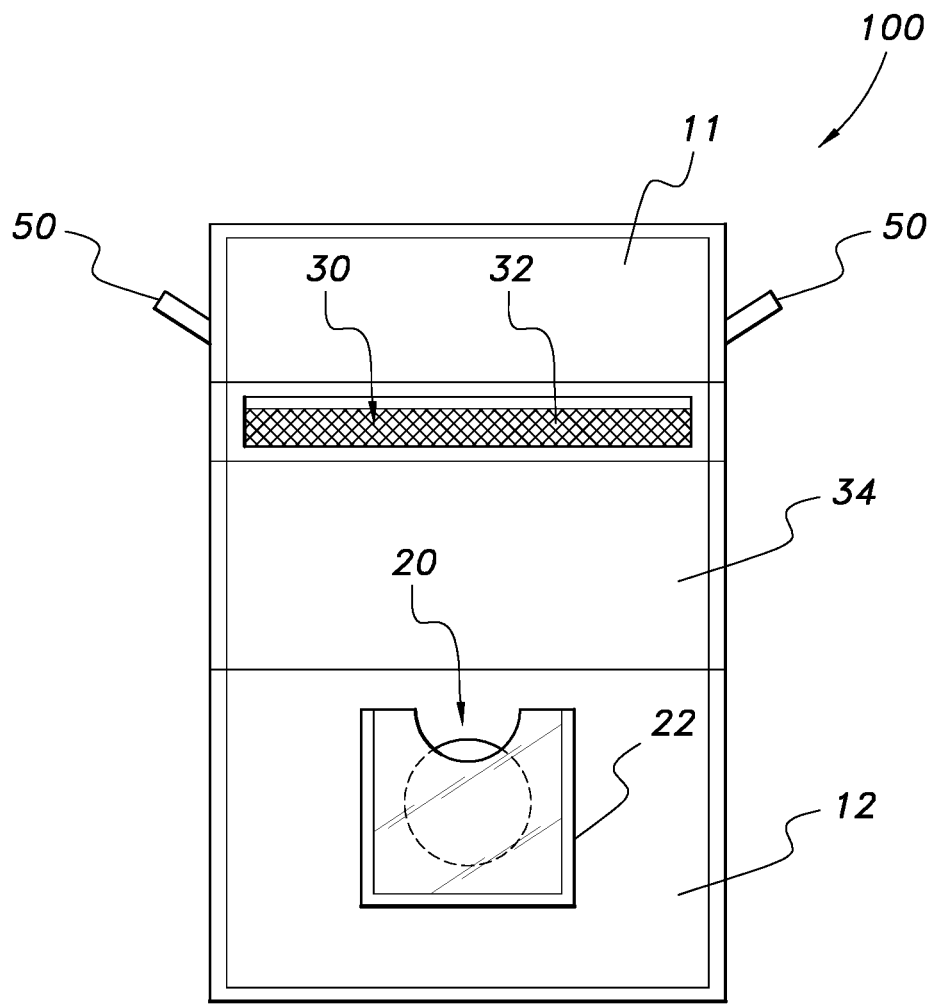
FIG. 6 is a front elevational view of the device of FIG. 1.

FIG. 6 is a front elevational view of the device 100 of FIG. 1.

Figure 7:
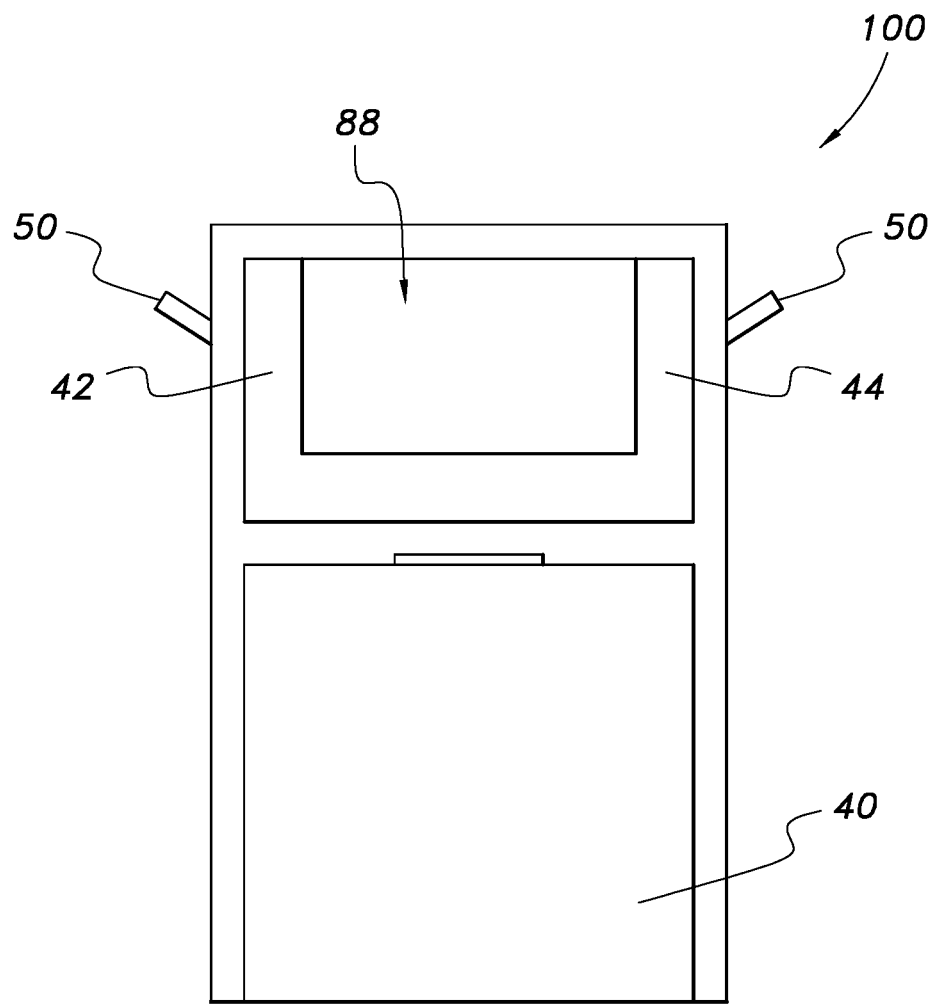
FIG. 7 a rear elevational view of the device of FIG. 1.

FIG. 7 a rear elevational view of the device 100 of FIG. 1.

Figure 8:
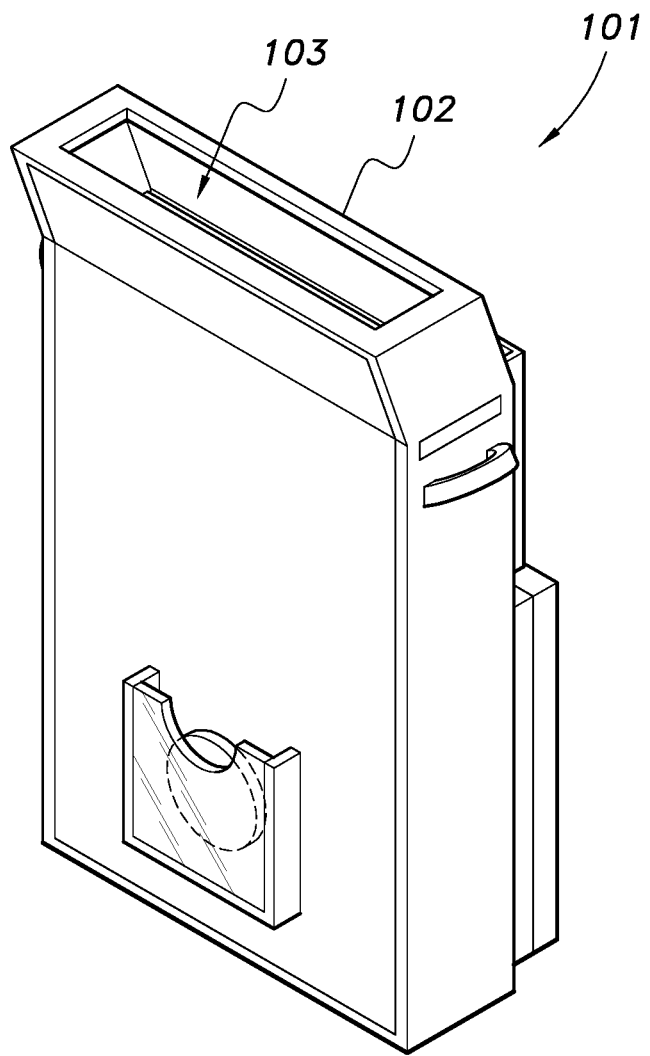
FIG. 8 is another embodiment of the device according to the present invention, having a top air flow opening.

FIG. 8 is another embodiment of the device 100, having a top air flow opening 103 and a top edge 102. In this embodiment, it is contemplated that the interior would be similar to that show in FIG. 4, but the fan 60 would be a sideways fan like a laptop computer fan, to push air out of the top of the device 100.

Figure 9:
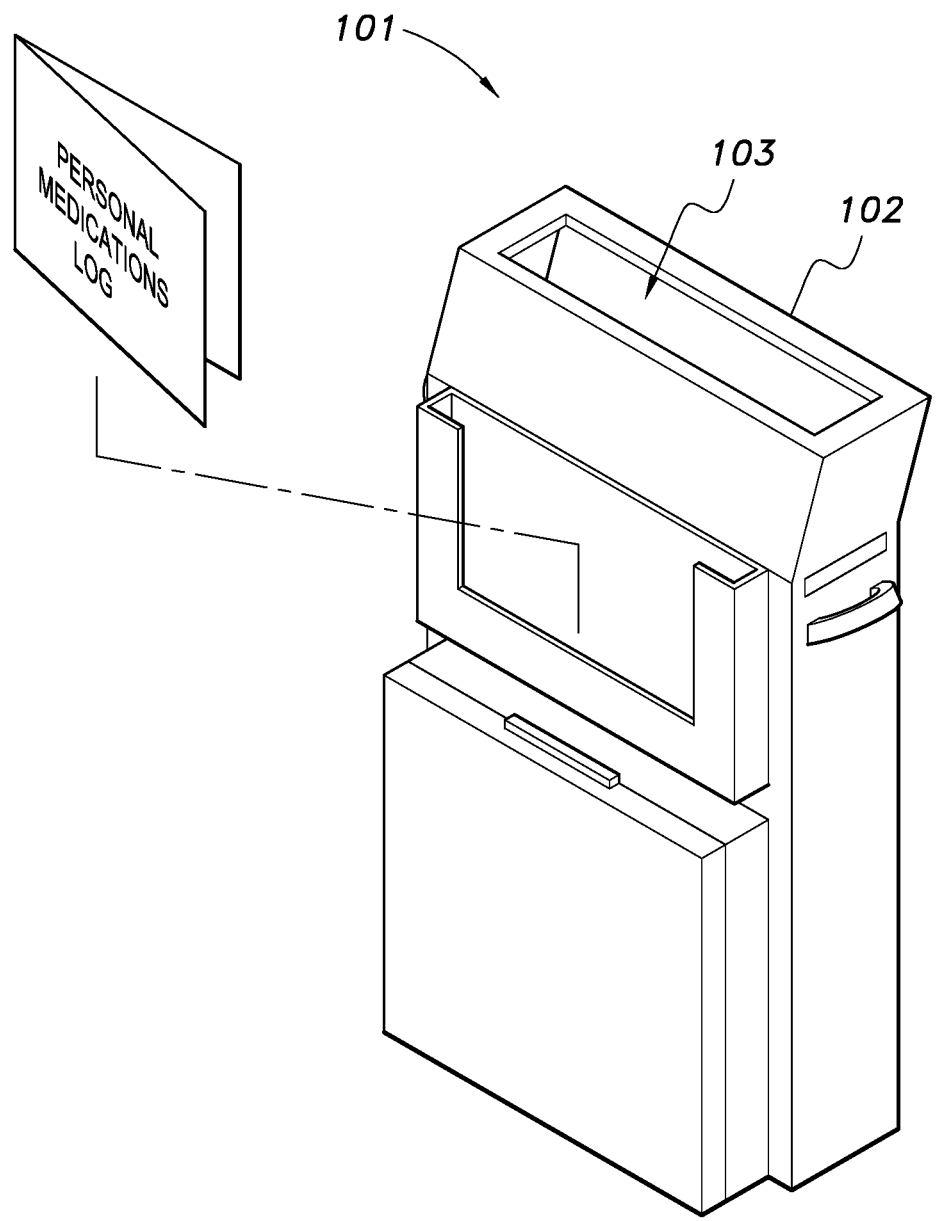
FIG. 9 is a rear elevational view of the device of FIG. 8.

FIG. 9 is a rear elevational view of the device 100 of FIG. 8.

Figure 10:
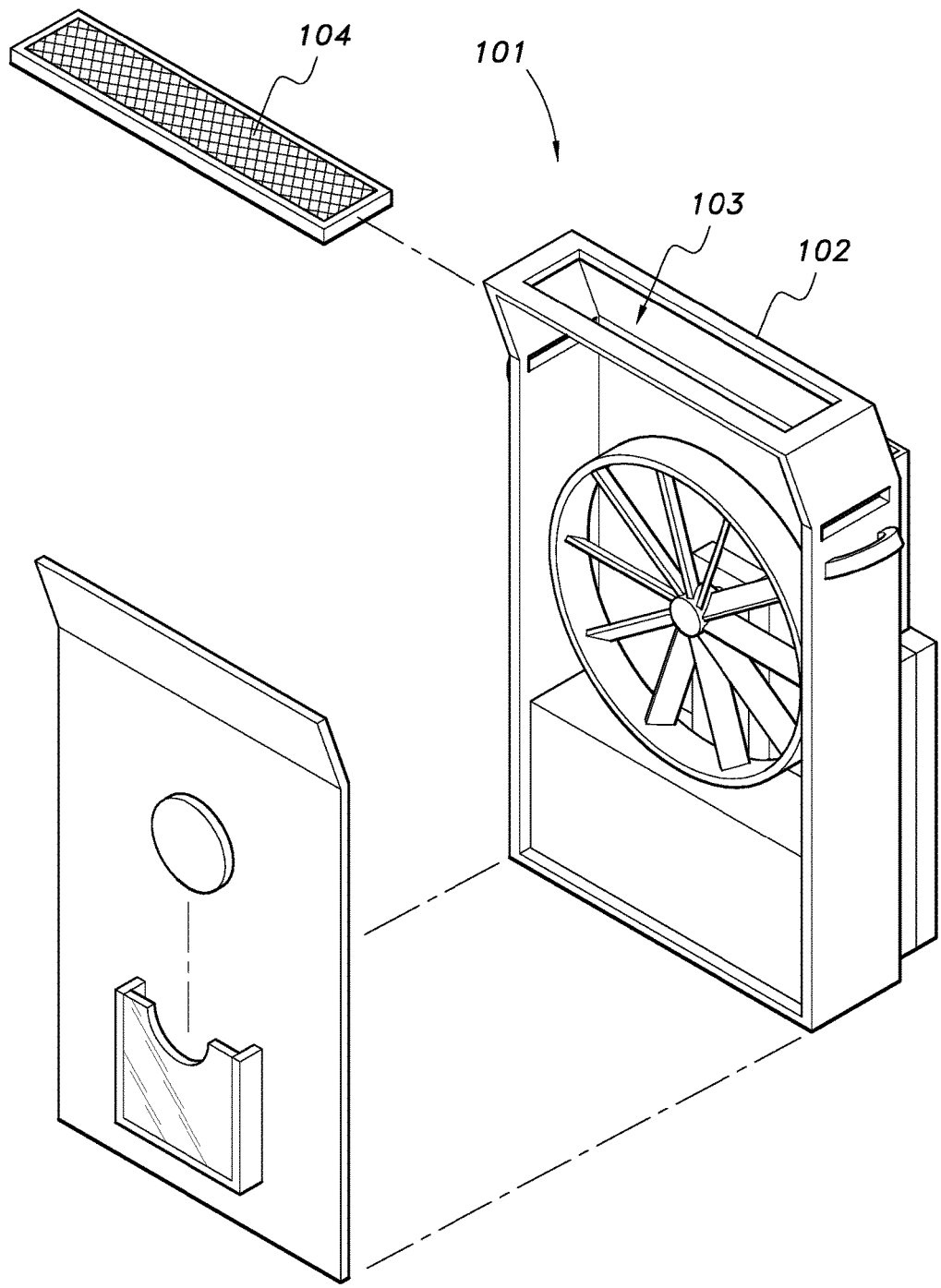
FIG. 10 is an assembly view of the device of FIGS. 8 and 9.

FIG. 10 is an assembly view of the device 100 of FIGS. 8 and 9.

Figure 11:
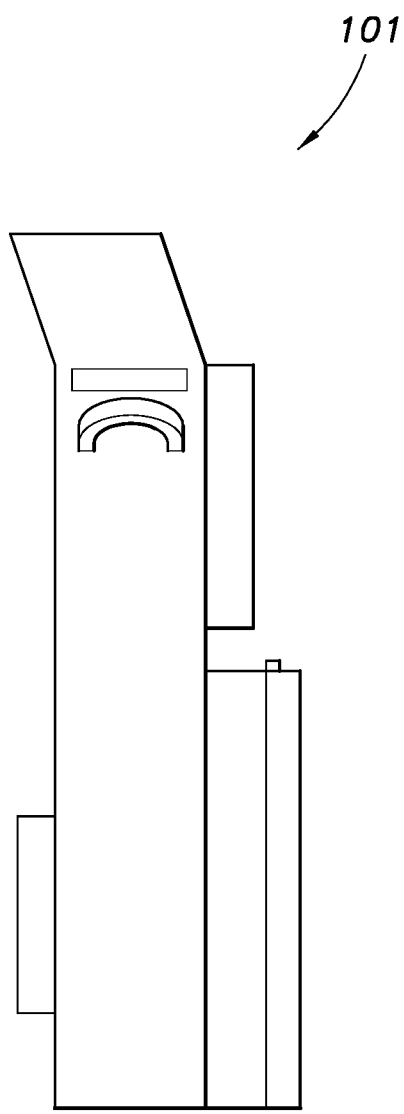
FIG. 11 is side elevational view of the device of FIG. 8 as viewed from the right.

FIG. 11 is side elevational view of the device 100 of FIG. 8 as viewed from the right.

Figure 12:
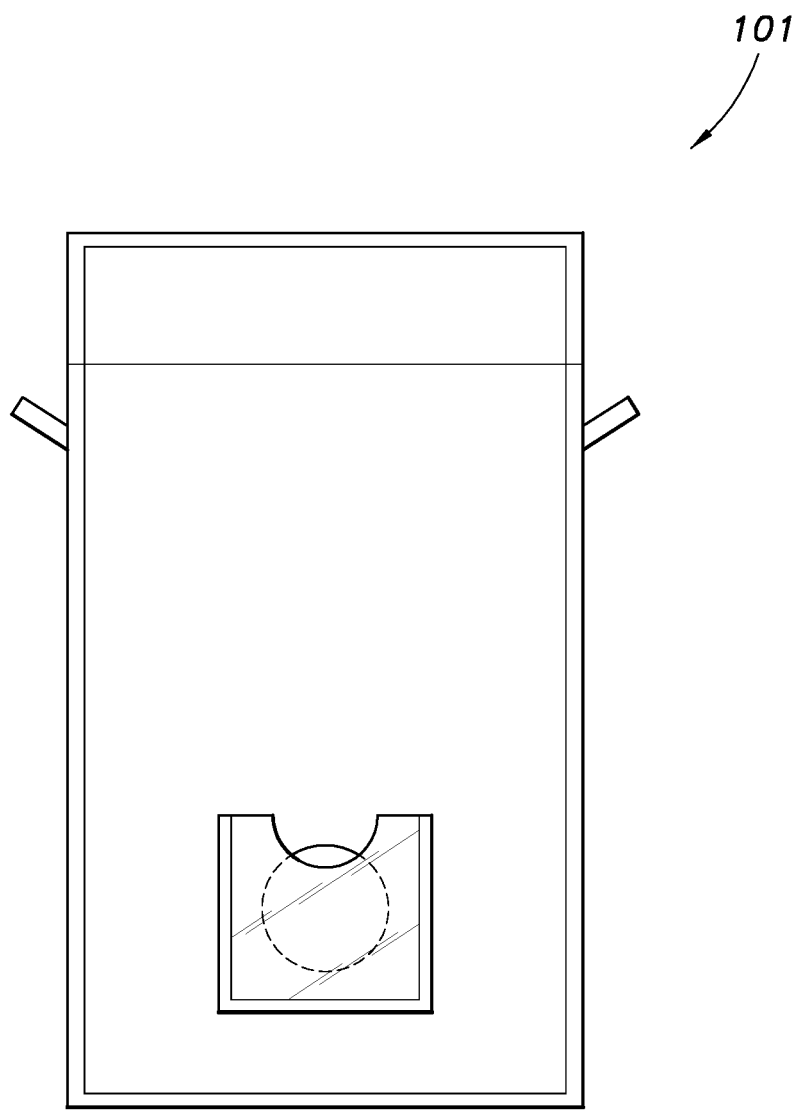
FIG. 12 is a front elevational view of the device of FIGS. 8-11.

FIG. 12 is a front elevational view of the device 100 of FIGS. 8-11.

Figure 13:
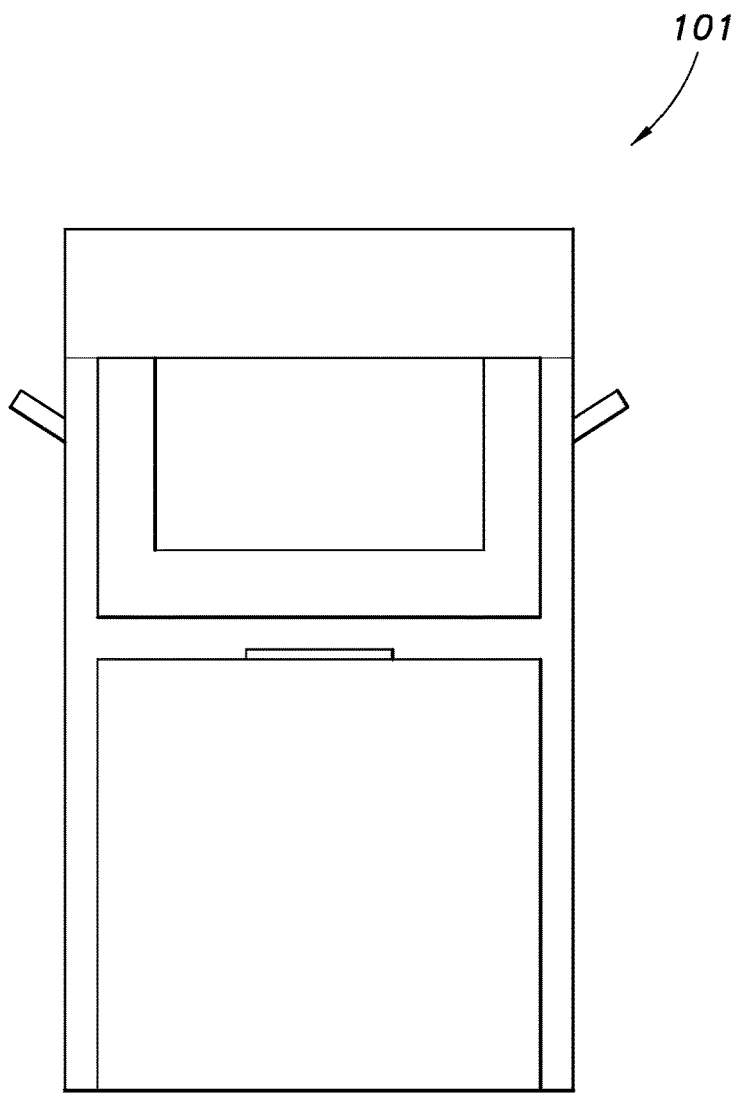
FIG. 13 is a rear elevational view of the device of FIGS. 8-11.

FIG. 13 is a rear elevational view of the device 100 of FIGS. 8-11.

Figure 14:
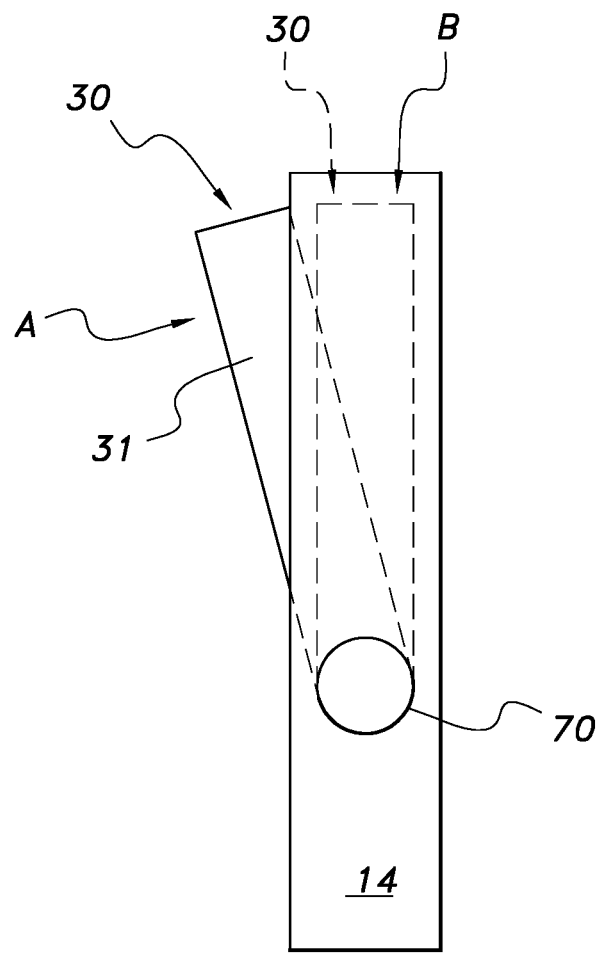
FIG. 14 is a schematic side view of a tiltable air outlet portion usable in the embodiment of FIGS. 1-7.

FIG. 14 is a schematic side view of a tiltable air outlet portion usable in the embodiment of FIGS. 1-7. The tiltable portion uses a pivot 70 to allow pivoting of the air outlet 30 between position A outside the housing 10 and position B inside the housing 10. A side wall 14 of the housing 10 is visible in this view. In this embodiment, the air outlet portion would include a pair of side walls 31 (only one of which is visible in FIG. 14). In this embodiment, the fan 60 would be carried by the tiltable portion and movable therewith, and is omitted from FIG. 14 for the sake of clarity. The pivot 70 can be a bearing or pin, and another such pivot 70 would be disposed on an opposite side from that shown. Tiltable outlets are known for directing air flow, and any such tiltable mechanism can be used which is within the ambit of skill of any one in the air flow control art.

Figure 15:
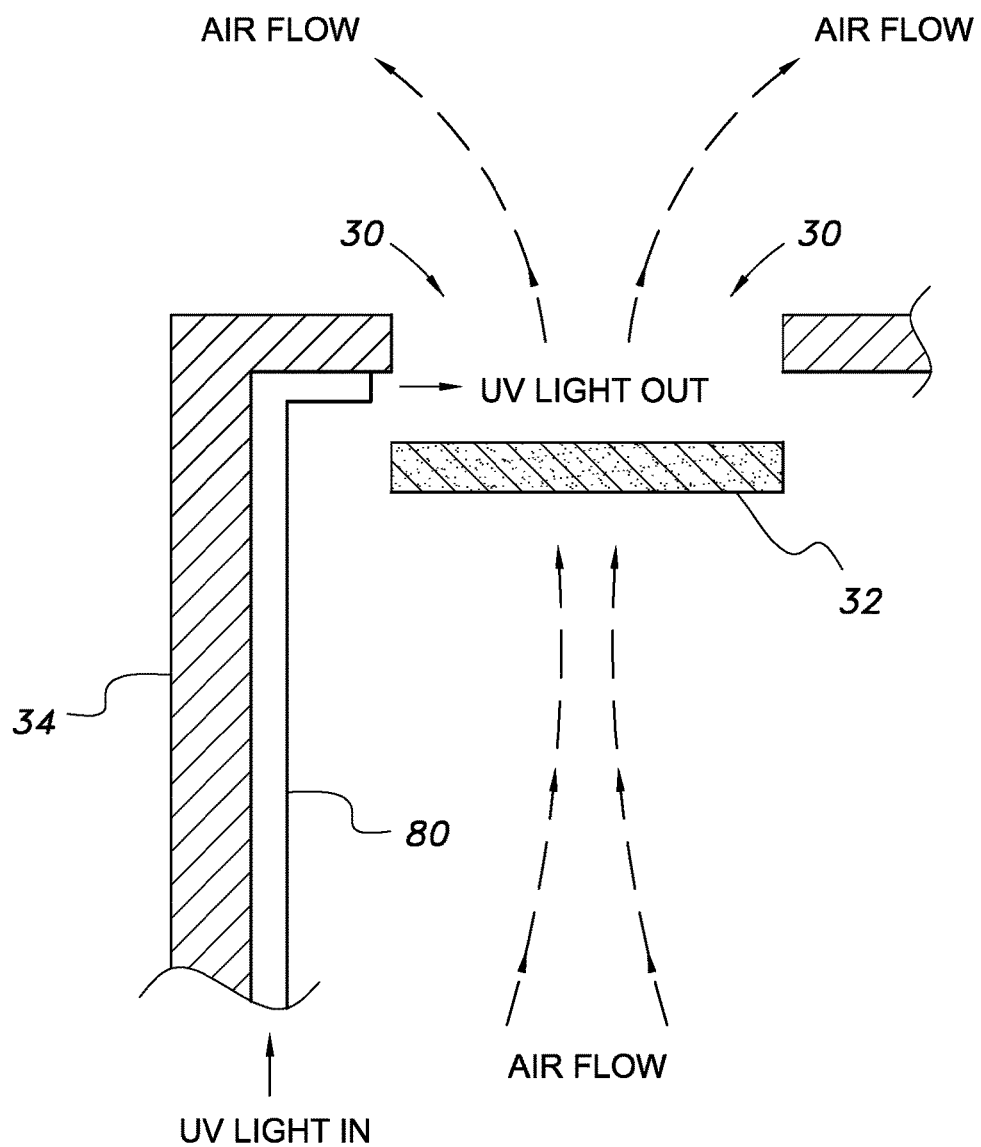
FIG. 15 is a schematic side sectional view of a further embodiment of the present invention, having a UV light guide to provide UV light to an air outlet.

FIG. 15 is a schematic side sectional view of a further embodiment of the present invention, having a UV light guide 80 adjacent to the lower panel 34. The UV light guide 80 is for providing UV light to the filtered air exiting from the air outlet portion 30. The UV light is directed such that it is generally parallel to the filter 32, so that the UV light is directed across the filter 32. Thus, the UV light does not shine outwardly of the device, and the UV light passing across the filter 32 is captured by the opposing portion of the housing 10 that exists opposite to the wall 34. The UV light therefore does not pose a hazard to the user, and the UV light source is safely located within the housing 10 where it is not subject to external impacts or breakage.

The UV light can be supplied, for example, by UV light from the UV bulb 420 shown in FIG. 4, or a separate UV source can be supplied. The light guide 80 can be a hollow mirrored channel, for example, or can be a solid thin material capable of carrying UV light. Alternatively, the light guide 80 can be composed of optical fiber materials bundled so as to form a sheet-like body, and the materials thereof are selected from those suitable for transmitting UV light. It is contemplated that the light guide 80 substantially spans the entire width of the panel 34 that coextends with the filter 34, so as to provide coverage of most or all of the air exiting from the filter 32. Additionally, the UV light can be focused prior to entering the light guide 80, to increase the intensity.

The invention being thus described, it will be evident that the same may be varied in many ways by a routineer in the applicable arts. Such variations are not to be regarded as a departure from the spirit and scope of the invention and all such modifications are intended to be included within the scope of the claims.

What is claimed is:

1. A portable device for providing filtered air in front of the face of a user when worn near a neck of the user, comprising:
    a housing having a front wall, a rear wall, a top wall, and side walls connecting said front wall and said rear wall to form an enclosure; said rear wall, said top wall, said side walls having respective interior portions such that said enclosure is bounded by said interior portions of said front wall, said rear wall, said top wall, and said side walls of said housing; and an air outlet portion disposed in said top wall; a filter member disposed in said air outlet portion; said side wall including a pair of opposed slots adjacent to said air outlet portion, said opposed slots being adapted to support said filter;
    said air outlet portion being disposed to direct air toward and in front of a face of a user when said housing is worn near the neck of the user;
    a UV light source disposed inside said housing, for providing UV light inside said housing to purify air moving inside said housing toward said filter member;
    a UV light guide member adapted to carry UV light, said UV light guide member having a first end disposed adjacent said UV light source and having a second end disposed inside said housing adjacent said filter member; said second end of said UV light guide member being disposed to direct light transversely to a direction of air flow exiting said filter member, whereby UV light is concentrated in a region of said air filter;
    a fan disposed inside said housing for urging air toward said air outlet portion and through said filter member, whereby filtered air purified by said UV light source is directed toward and in front of the face of the user;
    said interior portions having a UV-reflecting coating;
    said UV light guide member being a solid thin material; and
    at least one air inlet disposed in said housing for enabling entry of air into said housing.

2. A portable device as claimed in claim 1, further comprising:
    a battery power source for powering said fan.

3. A portable device as claimed in claim 1, further comprising:
    a CO detector disk mounted on a outside wall of said housing, for providing a visible color change when CO is detected.

4. A portable device as claimed in claim 1, further comprising:
    a pill box mounted on an outside wall of said housing.

5. A portable device as claimed in claim 1, further comprising:
    a holder for a personal medications log mounted on a rear wall of said housing, and a personal medications log insertable therein.

* * * * *